United States Patent [19]

Bakke

[11] Patent Number: 4,847,470

[45] Date of Patent: * Jul. 11, 1989

[54] ELECTRIC BLOOD WARMER UTILIZING METALLIC RIBBON FLOW CARTRIDGE AND LOW THERMAL MASS HEATING UNITS

[76] Inventor: Allan P. Bakke, 609 19th Ave. SW., Rochester, Minn. 55902

[*] Notice: The portion of the term of this patent subsequent to Nov. 1, 2005 has been disclaimed.

[21] Appl. No.: 132,193

[22] Filed: Dec. 14, 1987

[51] Int. Cl.$^4$ .......................... H05B 1/02; F24H 1/12; A61M 5/14; B67D 5/62

[52] U.S. Cl. .................................. 219/299; 128/399; 165/170; 219/302; 219/328; 222/146.5; 604/114

[58] Field of Search .................. 219/296–299, 219/301–309, 328, 330, 331; 128/399, 400; 604/113, 114; 165/170; 222/146.5

[56] References Cited

U.S. PATENT DOCUMENTS

| | | | |
|---|---|---|---|
| 1,087,518 | 2/1914 | Wallman | 219/336 |
| 3,399,536 | 9/1968 | Walz | 165/170 X |
| 3,475,590 | 10/1969 | Pins | 219/302 |
| 3,485,245 | 12/1969 | Lahr et al. | 128/272 |
| 3,492,460 | 1/1920 | Reich | 219/291 |
| 3,590,215 | 6/1971 | Anderson et al. | 219/298 |
| 3,612,059 | 10/1971 | Ersek | 219/299 X |
| 4,057,918 | 11/1977 | Zeier | 219/302 X |
| 4,117,881 | 10/1978 | Williams et al. | 219/299 X |
| 4,167,663 | 9/1979 | Granzow et al. | 219/497 |
| 4,309,592 | 1/1982 | Le Boeuf | 219/299 |
| 4,314,143 | 2/1982 | Bilstad et al. | 219/497 |
| 4,356,383 | 10/1982 | Dahlberg et al. | 219/302 |
| 4,358,664 | 11/1982 | Kronseder | 219/299 |
| 4,473,739 | 9/1984 | Scheiwe et al. | 219/302 |
| 4,782,212 | 11/1988 | Bakke | 219/299 |

FOREIGN PATENT DOCUMENTS

| | | | |
|---|---|---|---|
| 26/3521 | 8/1927 | Australia | 219/299 |
| 15338 | 7/1929 | Australia | 219/299 |
| 2530928 | 1/1977 | Fed. Rep. of Germany | 219/296 |
| 2632985 | 1/1978 | Fed. Rep. of Germany | 219/301 |
| 2640134 | 3/1978 | Fed. Rep. of Germany | 219/299 |
| 573313 | 4/1946 | Netherlands | 165/170 |
| 90221 | 9/1937 | Sweden | 165/170 |

Primary Examiner—Anthony Bartis
Attorney, Agent, or Firm—Wayne O. Hadland

[57] ABSTRACT

An apparatus for warming blood from storage to physiologic temperatures at transfusion rates up to 160 milliliters per minute includes a flat metal cartridge formed by a pair of thin generally rectangular planar members spaced slightly apart in parallelism and sealed at their peripheral edges to define one or more thin constant-width and uniform thickness ribbon-like conduits through which blood flows from an inlet port to an outlet port at opposite ends of the cartridge. An inlet chamber and an outlet chamber, each defined by an elongated recess in one of the planar members, communicates the entire width of a corresponding end of each conduit with the inlet and outlet ports to establish uniform blood flow across each full conduit width. The cartridge is clamped between a pair of heating units, each unit having a low thermal mass and uniform heat distribution and including a thin flat metal plate having one surface disposed to clamp against the cartridge and the opposite surface bonded to a thin etched-foil electric heater, which respond rapidly to changes in blood flow rate without excessive temperature overshoot. The heating units are controlled in response to temperature sensors embedded in one of the heating units closely adjacent the clamping surface thereof and positioned to lie closely adjacent to the cartridge outlet chamber.

7 Claims, 4 Drawing Sheets

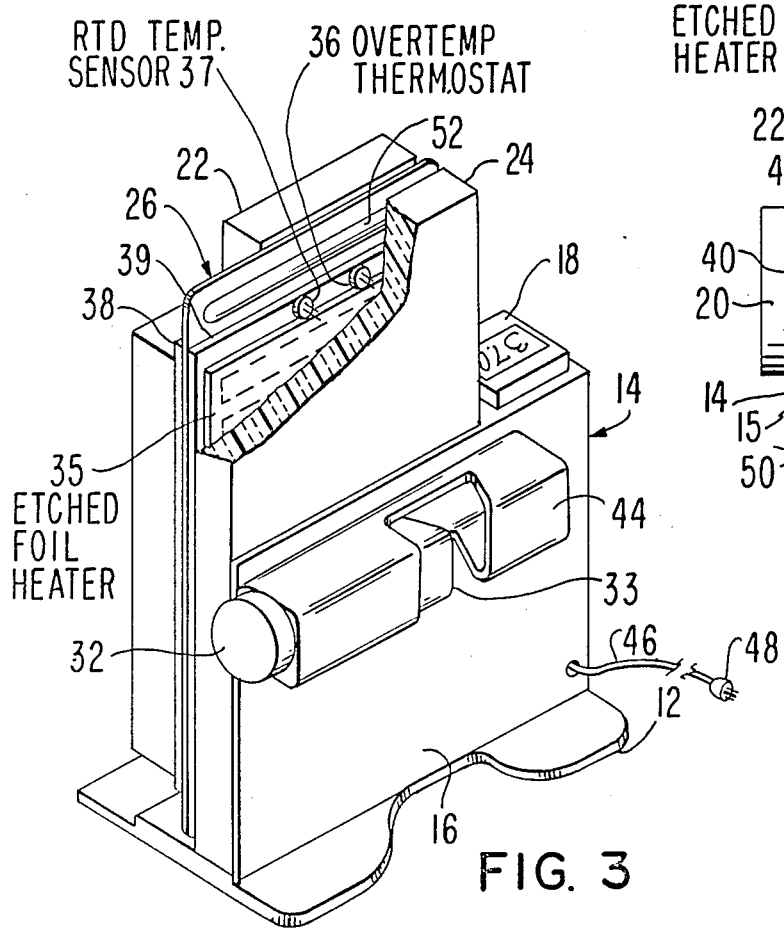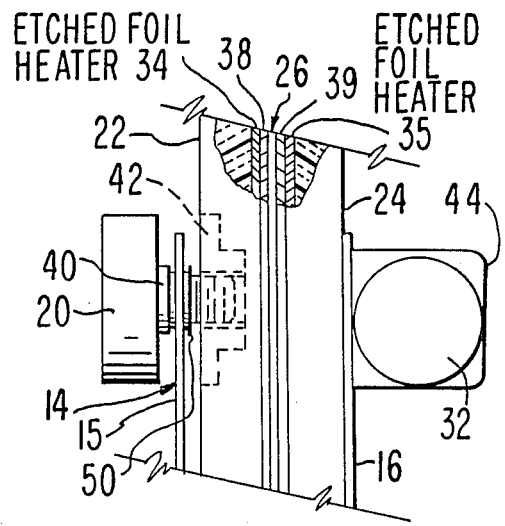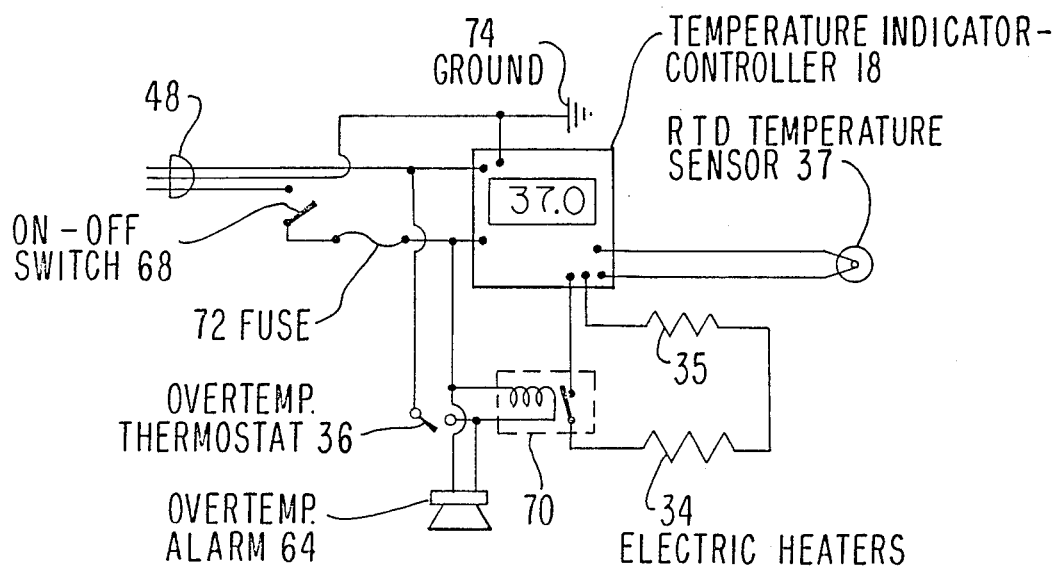

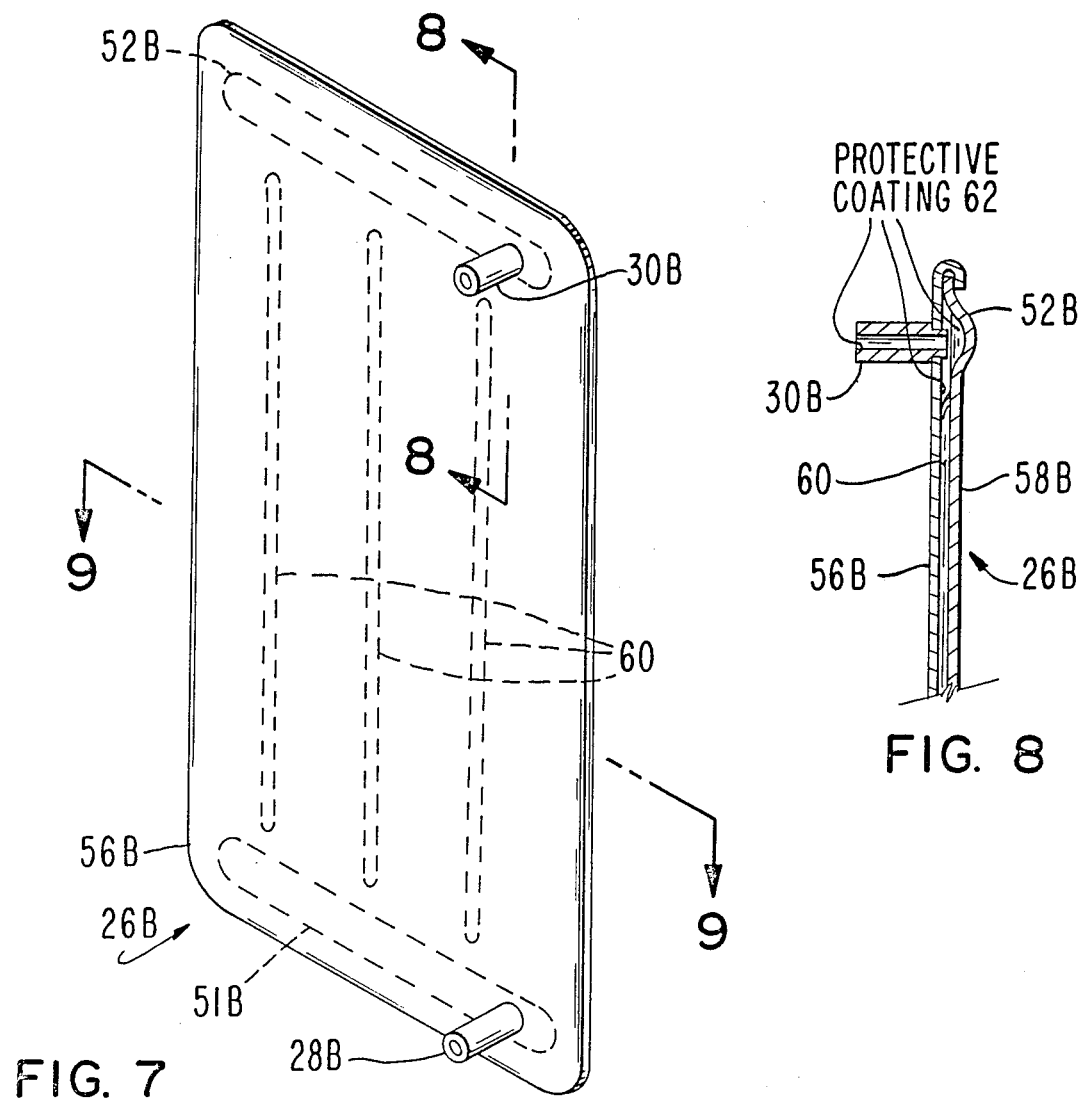
FIG. 7
FIG. 8
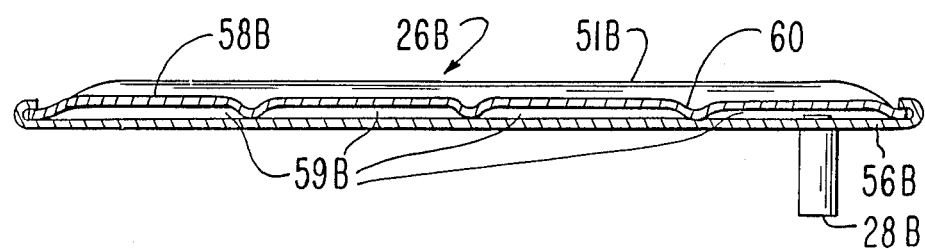
FIG. 9

ELECTRIC BLOOD WARMER UTILIZING METALLIC RIBBON FLOW CARTRIDGE AND LOW THERMAL MASS HEATING UNITS

BACKGROUND—FIELD OF INVENTION

The present invention generally relates to devices for heating liquids, and more particularly to a compact ribbon-flow cartridge-type blood warmer capable of heating blood or other fluids for infusion from refrigerated storage temperature to physiologic temperature at flow rates varying from zero to those required during massive transfusion.

Blood is generally stored at a temperature near 4° Celsius. Prior to intravenously infusing refrigerated blood into the human body, it should be warmed to near physiologic temperature (32° to 37° Celsius). During massive transfusions flow rates as high as 160 milliliters per minute may be required.

BACKGROUND—CROSS-REFERENCE TO RELATED PATENT

This application is related to the following U.S. patent.
U.S. Pat. No. 4,782,212
Issue Date—Nov. 1, 1988
Inventor—Allan P. Bakke
Title—Electric Blood Warmer Utilizing a Metallic Ribbon-Flow Cartridge

BACKGROUND—DESCRIPTION OF PRIOR ART

Various kinds of blood warmers presently exist. Most utilize a flexible plastic container or conduit for the blood being heated, such as plastic tubing immersed in a warm water bath or a plastic bag or pouch sandwiched between heating plates. Usually the heated flow path is quite long (in the case of tubing) or the flow is otherwise intentionally restricted (in the pouch-type heaters) to promote uniform heating of the liquid along the heated flow path.

Flexible plastic blood containers or conduits need to have substantial wall thickness (for example, a minimum of 0.1 millimeter or 4 mils is recommended for the Le Boeuf warmer, U.S. Pat. No. 4,309,592) in order to prevent both rupture and, in the case of bag-type units, localized wrinkling or folding of the bag between the heating plates which would impede fluid flow. Because plastic materials are good insulators but in general poor conductors of heat, the necessity of having relatively thick plastic walls imposes a requirement of large heating areas and/or fairly high heating plate temperatures in order to obtain an adequate rate of heat transfer to the blood. High heating plate temperatures impose a risk of damaging blood by overheating which hemolyzes the red blood cells; large heating areas imply large priming volumes with a consequent waste of blood, as well as large physical size. Long or restricted flow paths increase the hydraulic resistance to fluid flow, thereby preventing high blood flow rates unless a high head of hydrostatic pressure is available. The water bath type blood warmers tend to heat fluids inadequately at high flow rates unless mechanical agitation is provided, and additionally are inconvenient to use because of the need to fill and maintain an open water bath in the operating room.

Consequently a need exists for a reliable, rugged, simple and compact blood warmer, having a small priming volume and low hydraulic flow resistance, which is able to warm refrigerated blood to physiologic temperature at from low to high transfusion rates.

SUMMARY OF THE INVENTION

The present invention provides a ribbon-flow cartridge-type blood warmer which overcomes the problems and satisfies the needs previously considered. As the blood being heated is contained in a metal cartridge, rather than a flexible plastic container, the risk of rupture and blood spillage is eliminated. The danger of overheating is reduced as a result of efficient heat transfer from the metal cartridge wall to the flowing blood, there being merely a very thin protective coating of a biocompatible material having relatively insignificant thermal insulating effects (due to the extreme coating thinness of approximately 0.04 mil, or about one percent of a flexible plastic pouch wall thickness) separating the blood from the warm metal wall surfaces. The blood enters and exits the thin wide heating channel via full-channel-width chambers at each end. The blood being heated hence uniformly flows as a thin wide ribbon between the warm cartridge walls, presenting a large surface area yet occupying a small (about 25 milliliters) priming volume, while flowing directly and efficiently from inlet to outlet over a short heated path characterized by low resistance to fluid flow.

Heating of the cartridge walls is accomplished by clamping the cartridge between thin metallic electrically-warmed heating plates, the temperature of which, sensed near the outlet of the cartridge, is controlled by a temperature indicator-controller. The heating plates are warmed by thin etched foil type electric heaters which apply a uniformly distributed heat flux to the entire area of the heating plates. The heating plates with respective foil heaters bonded or vulcanized in place are mounted on and supported by thick, rigid heat insulator blocks. The assembled combination of one heating plate, one electric heater, and one insulator block is called a heating unit. One heating unit is fixed while the other is movable to permit easy insertion and clamping of the blood warming cartridge.

Analysis of heat transfer to the blood in a wide, rectangular flow channel having a constant temperature of the outside (i.e. heated, unwetted side) of the walls results in the following equation:

$$(T_w - T_m)/(T_w - T_i) = e^{[-7k_f(a/b) \times ]/[mC_p(1 + 3.5(k_f/k_w)(t/b))]}$$

Where:
$T_w$ = Temperature of the outer (unwetted) surface of the wall of the flow channel.
$T_m$ = Mean temperature of the fluid at any station x.
$T_i$ = Inlet temperature of the cold blood.
x = Distance from inlet.
a = Width of flow channel.
b = Depth of flow channel (i.e., distance between the heating plates).
m = Mass flow rate of blood.
$C_p$ = Specific heat of blood.
$k_f$ = Thermal conductivity of blood.
$k_w$ = Thermal conductivity of wall.
t = Wall thickness.

As the exponent in the above equation increases in absolute value, the mean blood temperature more closely approximates the wall temperature and thermal performance is improved. Thus for a fixed length and flow rate, the quantity a/b should be maximized, indicating the desirability of a wide channel with very closely spaced walls. It is also apparent, as one would expect, that cartridge walls of high thermal conductivity improve thermal performance.

This improved blood warmer has a small priming volume, provides excellent thermal performance (as a consequence of reducing the plate spacing "b", having uniformly wide channel width "a", and having metal walls of good thermal conductivity, and also exhibits a low hydrostatic pressure drop across the warmer cartridge.

The very high heat transfer efficiency of the cartridge of this invention, combined with the thin metal heating plates, thin etched foil electric heaters of low thermal inertia backed by rigid insulator blocks produces a plurality of unexpected improvements in performance and simplicity in the instant invention compared with previous art. In both zero flow and maximum flow conditions, the outlet regions of the heating plates attain the highest temperature (the same as the inlet in the case of zero flow). The very high thermal efficiency of the cartridge, the very low thermal mass of the electric heaters and heating plates and the uniform heat flux distribution of the etched foil electric heaters permit a single temperature sensing means at the outlet region of the heating plate to control the electric heaters without excessive temperature overshoot even when flow is abruptly reduced from maximum flow to zero. A commercially available temperature indicator-controller may be employed which provides proportional band control, zero voltage crossing switching and triac switching on and off of the heater power output. A separate, independent overtemperature thermostat is located near the outlet to turn off the heaters if outlet temperature exceeds a fixed safe upper limit.

Accordingly, the present invention relates to an apparatus for warming blood, and consists primarily of a hollow flat metal container called a cartridge in which blood is warmed as it passes through, the cartridge being clamped between two thin metal heating plates of high thermal conductivity. The heating plates are heated by thin etched foil type electric heaters of low thermal mass controlled by a temperature sensing means located in the outlet region of the heating plate very close to the cartridge surface and a temperature indicator-control means.

DESCRIPTION OF THE DRAWINGS

FIG. 2 is a partial side view partially in section showing the cartridge clamping mechanism as indicated by section line 2—2 shown in FIG. 1.

FIG. 3 is a partially sectioned isometric back view of the preferred embodiment of the present invention depicted in FIG. 1.

FIG. 7 is an isometric view of an alternative design of a disposable blood containing cartridge.

FIG. 8 is a sectional view through the cartridge taken along the vertical section line 8—8 shown in FIG. 7.

FIG. 9 is a sectional view through the cartridge taken along the horizontal section line 9—9 shown in FIG. 7.

FIG. 10 is a schematic diagram of the electrical circuits and elements employed in the present invention.

DESCRIPTION OF THE PREFERRED EMBODIMENT

Figure 1:
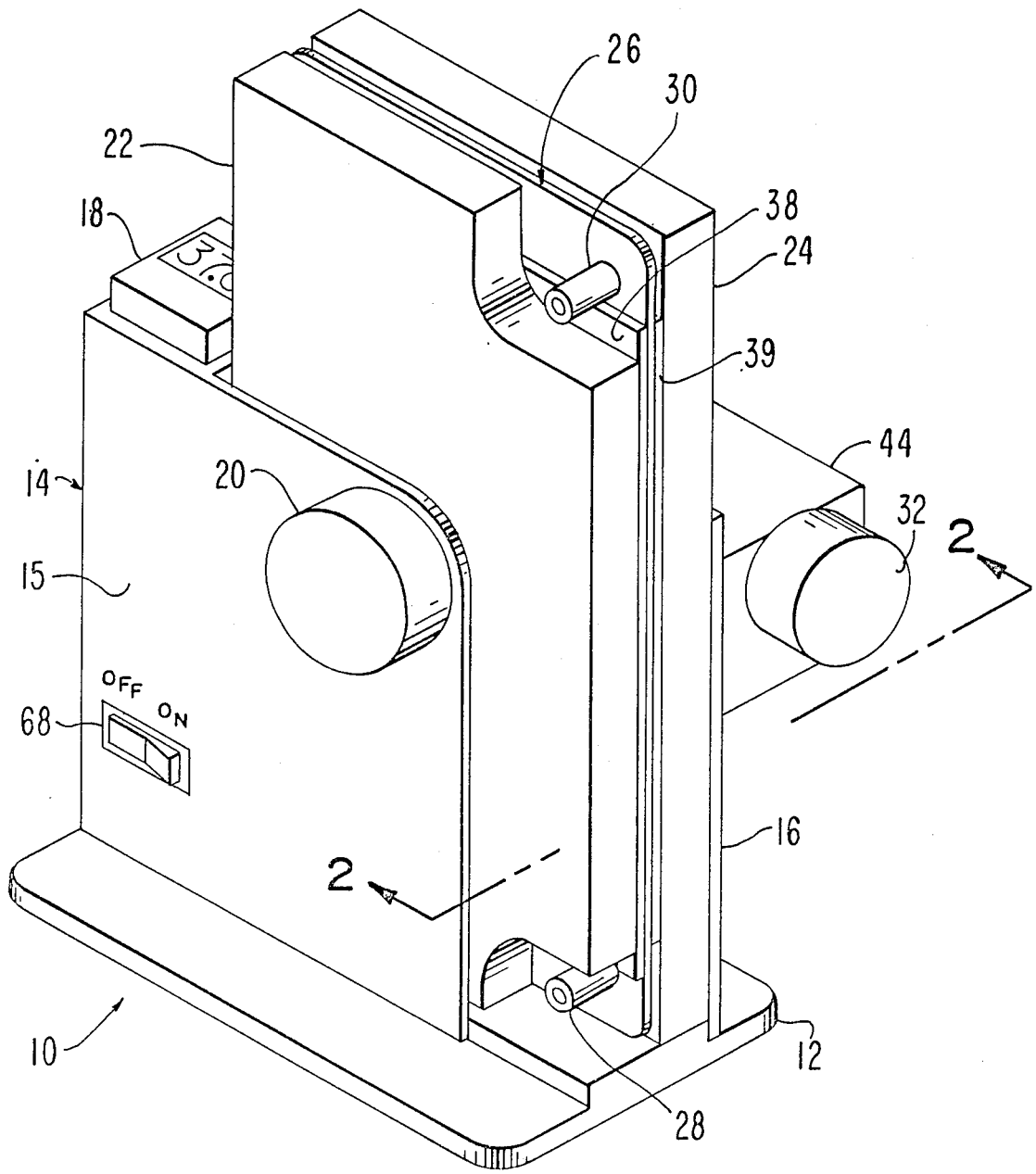
FIG. 1 is an isometric front view of the preferred embodiment of the present invention, a ribbon-flow cartridge-type dry heat blood warmer.

Referring now to the drawings, and more particularly to FIG. 1, there is shown a ribbon-flow cartridge-type blood warmer apparatus, generally designated warmer apparatus 10, which comprises the preferred embodiment of the present invention. The apparatus 10 includes a base 12 which allows apparatus 10 to rest on a flat surface with great stability. The housing 14 is securely attached to base 12 and serves to mechanically support the fixed insulator block 24, the temperature indicator-controller 18, the support pole clamping device 44, and the cartridge clamping shaft 40 shown in FIG. 2.

Referring again to FIG. 2, the cartridge clamping shaft 40 is restrained axially by having a larger diameter outside the housing front plate 15, and by a cartridge clamping shaft retainer 50 inside housing front plate 15. The threaded portion of cartridge clamping shaft 40 engages the threaded insert 42 which is firmly affixed to a recess in the movable insulator block 22 by mechanical fastening means, such as epoxy adhesive or screws. Rotation of cartridge clamping knob 20 which is affixed to cartridge clamping shaft 40 moves the movable insulator block 22 toward (or away from) fixed insulator block 24, thus providing means for clamping the blood warming cartridge 26 between movable heating plate 38 and fixed heating plate 39. Movable electric heater 34 is of the thin etched foil type and is bonded or vulcanized to movable heating plate 38; plate 38 is affixed to movable insulating block 22 which provides rigidity, support, and thermal insulation; the heater, the plate, and the block together comprise the movable heating unit. Similarly, fixed heating plate 39, fixed electric heater 35, and fixed insulator block 24 are firmly fastened together, comprising the fixed heating unit. Fixed insulator block 24 is affixed to housing rear plate 16 with screws or other mechanical fastening means. Insulator blocks 22 and 24 may be made of high density structural plastic foam, wood, or other rigid thermal insulating material. Housing 14 may be aluminum or other metal. Cartridge clamping knob 20 may be aluminum, other metal or plastic. Cartridge clamping shaft 40 may be aluminum, steel or other metal. Threaded insert 42 may be metal or plastic.

Referring to FIG. 3, support pole clamping device 44 provides means for clamping warmer apparatus 10 to a vertical support or IV pole. Knob 32 is connected to clamping device 44 and slide 33 by means such that rotating knob 32 clockwise causes slide 33 to advance and grip a pole inserted into the gap in clamping device 44. A recess in base 12 allows clearance for a vertical support pole.

Referring to FIG. 3, overtemperature thermostat 36 is located in the outlet region of fixed heating plate 39 in a recess which places thermostat 36 in very close proximity to the surface of said plate 39 which is in contact with the outer surface of blood warming cartridge 26. RTD temperature sensor 37 is located near thermostat 36, and similarly in a recess in fixed heating plate 39. Wires from overtemperature thermostat 36 and RTD temperature sensor 37 are shown schematically in FIG. 10.

Figure 4:
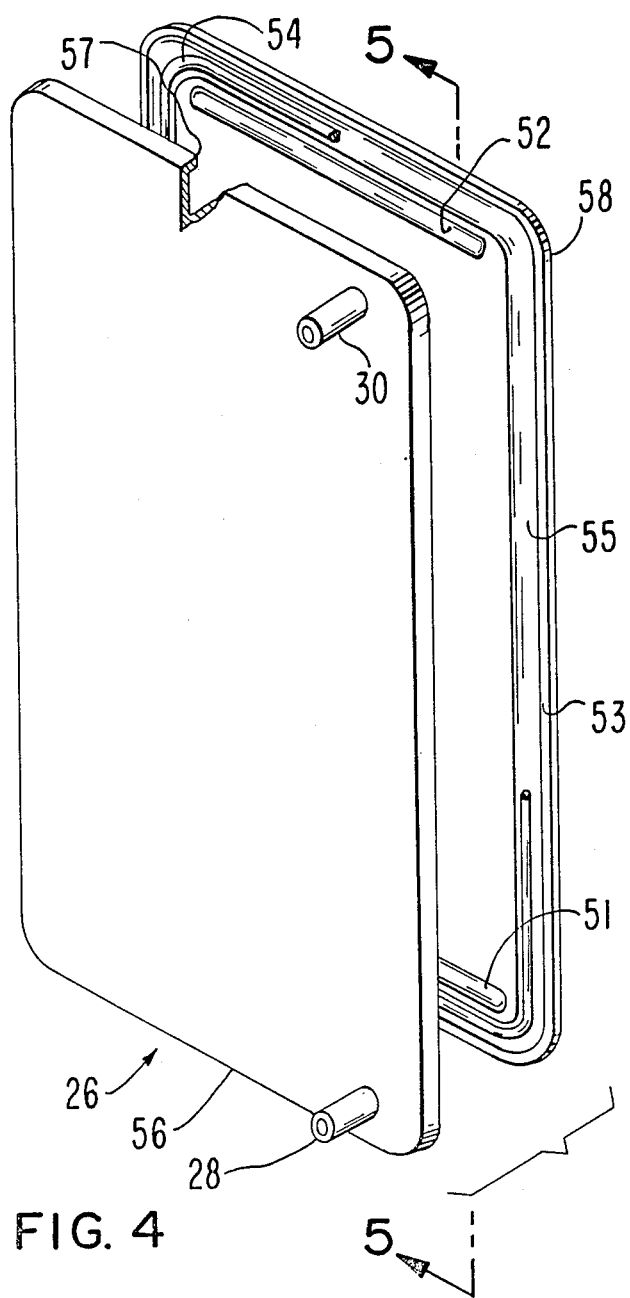
FIG. 4 is an exploded view of the blood warming cartridge.
Figure 5:
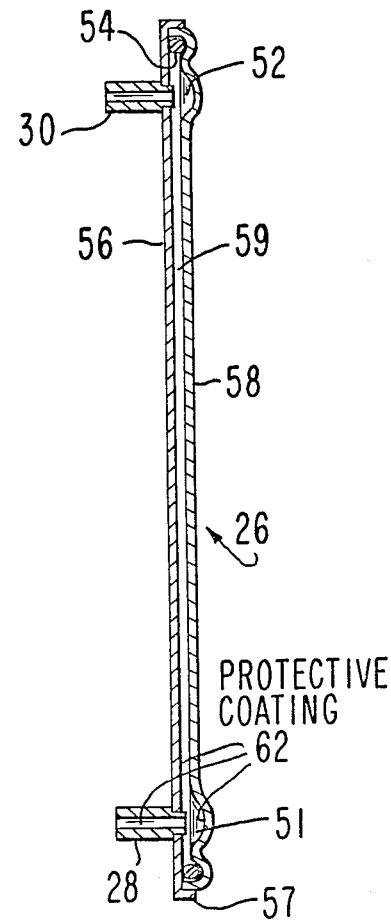
FIG. 5 is a non-exploded sectional view through the cartridge taken along the vertical section line 5—5 shown in FIG. 4.

The blood warming cartridge 26 is shown in FIG. 4 in an exploded view; FIG. 5 is a non-exploded sectional view through the inlet tube 28 and the outlet tube 30 of cartridge 26. Cartridge 26 is made up of two major components; a front plate 56 and a back plate 58. Blood inlet tube 28 and outlet tube 30 are permanently attached to front plate 56; FIG. 5 shows the tubes as having been simply pressed into through-holes in said plate, thereby forming inlet and outlet ports for blood to enter and leave the interior of the cartridge. The periphery of front plate 56 is turned up to form a lip 57 that insures proper alignment with back plate 58. The periphery of back plate 58 is turned up to form a rim 53 which fixes the distance between the opposed inner surfaces of plates 56 and 58 when they are pressed together as shown in FIG. 5, thereby forming a narrow flow conduit 59. A gap distance of about 0.8 mm was used for the prototype apparatus. A peripheral groove 55 is formed just within the rim 53 of back plate 58 to receive perimeter seal 54. Two horizontal trough-shaped recesses forming chambers 51 and 52, located just inboard of the perimeter seal 54 and opposite inlet and outlet tubes 28 and 30, are formed into and extend entirely across the bottom and top width of back plate 58. Chambers 51 and 52 serve to distribute flow over the width of cartridge 26 to promote uniform ribbon flow. For the prototype apparatus the front plate 56 and the back plate 58 were made of approximately 40 mil thick aluminum. Other materials with very high thermal conductivity which are easily formed, such as alloys of copper, could also be used.

Figure 6:
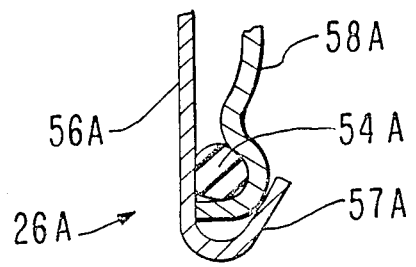
FIG. 6 shows an alternative non-separable formed edge design (as compared to the separable edge design as shown in FIG. 5).

The perimeter seal 54 is made from a resilient biocompatible elastomer such as silicone rubber. All components of cartridge 26 must be able to withstand temperatures reached in the steam sterilization autoclaving process. The cartridge embodiment shown in FIG. 4 and FIG. 5 has separable front and back plates 56 and 58 which may be taken apart, cleaned and sterilized, and re-used. The cartridge may also be made in a disposable, inseparable version, cartridge 26A, by simply crimping the lip 57A of front plate 56A over the rim peripheral edge of back plate 58A; this construction detail is shown in FIG. 6.

Another embodiment of the blood warming cartridge is shown as cartridge 26B in FIGS. 7, 8, and 9. The front plate 56B is a thin flat metal sheet. The back plate 58B has its edges formed slightly offset to establish the desired plate separation. The edges of front plate 56B are rolled over the offset edges of back plate 58B to mechanically join and seal the plate edges forming a non-separable, disposable cartridge as shown in FIGS. 8 and 9. Horizontal trough-shaped recesses forming chambers 51B and 52B are formed into back plate 58B opposite inlet and outlet tubes 28B and 30B to distribute blood across the cartridge width to promote uniform ribbon flow through the heated narrow flow conduits 59B. Longitudinal ridges 60 are formed into the back plate 58B to preserve proper separation gap between front and back plates 56B and 58B. The contact between ridge peaks of the back plate and the inner surface of front plate 56B may be reinforced by adhesive bonding, spot welding, or may be unattached. Remaining construction details of cartridge 26B are similar to cartridge 26. The wetted interior surfaces of plates 56 and 58, 56A and 58A, 56B and 58B (which includes interior surfaces of tubes 28 and 30, 28A and 30A, 28B and 30B) may be coated with a very thin protective coating 62 of a biocompatible material, such as a one micron (0.04 mil) thick coating of Union Carbide Corporation Type C parylene (polymonochloro-para-xylylene) thermoplastic polymer coating.

FIG. 10 is a schematic diagram of the electrical components and wiring of the apparatus 10. Grounded plug 48, connected to power cord 46, provides 110 volt, 60 Hz power obtained from a grounded wall source. On-off switch 68 interrupts power to the apparatus by choice of the operator. Fuse 72 opens the power supply circuit if excessive current flows. Ground 74 connects electrically to housing 14 as well as to heating plates 38 and 39, and to the ground connection of temperature indicator-controller 18. Temperature indicator-controller 18 is a commercially available device with digital temperature display, employing on-off or proportional band control of electric heaters 34 and 35 with zero crossing electronic switching of a triac to control the supply of power to the electric heaters 34 and 35. A resistive temperature device (RTD) sensor 37 is used to measure temperature of the cartridge (and blood) near the outlet. Controller 18 maintains outlet temperature at approximately 37° Celsius by appropriately energizing electric heaters 34 and 35. Failure of RTD sensor 37 results in an "upscale" or high temperature indication, internal alarm, and shut-off of the electric heaters 34 and 35 by the controller 18.

A completely separate safety shut-off for excessive temperature is comprised of overtemperature thermostat 36 (which is in thermal contact with outlet region of cartridge 26), overtemperature relay switch 70, and overtemperature alarm 64. Overtemperature thermostat 36 closes at a preset maximum allowable temperature known to be safe for blood (approximately 44° Celsius), energizing both alarm 64 and relay switch 70 which interrupts power to heaters 34 and 35.

In operation cold blood under slight pressure enters cartridge 26 at inlet tube 28 via such means as flexible IV tubing which connects to said tube 28. The flow spreads into inlet chamber 51 and then moves as a thin wide ribbon through the heated narrow flow conduit 59 between cartridge front plate 56 and back plate 58 until it enters outlet chamber 52, from whence the warmed blood exits the cartridge at outlet tube 30.

From the foregoing description, it will be apparent that the invention disclosed herein provides a novel and advantageous blood warmer design. As will be understood by those familiar with the art, the invention may be embodied in other specific forms without departing from the spirit or essential characteristics thereof. For example, a two-stage control system could be employed, sensing and controlling both at the outlet and at a point part way through the warmer, thus markedly further improving apparatus efficiency, albeit at the cost of a second control means.

I claim:

1. An apparatus for warming blood for transfusion, comprising:
   a fluid-impervious rigid flat metal cartridge defining an enclosed cavity of small volume, having an inlet port and an outlet port at opposite ends thereof, the interior of said cartridge being compatible with the temporary storage of blood, the exterior of said cartridge having two flat heatable surfaces;
   said cartridge including a pair of thin metal generally rectangular planar members spaced slightly apart and in parallelism with each other, said members being sealed together at their edges to define an unobstructed constant-width and uniform-thickness thin ribbon-like conduit for fluid between the interior surfaces of said members;

said cartridge further including a trough-shaped elongated recess defining an inlet chamber communicating with said inlet port, and a trough-shaped elongated recess defining an outlet chamber communicating with said outlet port, each chamber running completely across and communicating with a corresponding end of said conduit, whereby fluid can uniformly flow into and out of said thin ribbon-like conduit across the full conduit width;

heating means including a pair of heating units each having a low thermal mass, a uniform heat flux distribution, and a flat clamping surface disposed to clamp against a corresponding flat outer surface of said cartridge between the inlet and outlet chambers thereof, for heating each of said cartridge heatable surfaces;

temperature sensing means embedded in one of said heating units closely adjacent to said clamping surface, positioned to lie closely adjacent to the outer surface of said cartridge immediately adjacent to the outlet chamber thereof; and control means responsive to said temperature sensing means to control the amount of heat supplied by said heating means to each cartridge flat side.

2. An apparatus for warming blood for transfusion as recited in claim 1, wherein:

said pair of heating units includes a movable heating unit and a fixed heating unit;

said heating means further includes means for supporting said heating units opposite one another with each said clamping surface being toward and parallel to the other; and said supporting means further includes means releasably clamping said cartridge between and against said supported heating units.

3. An apparatus for warming blood for transfusion as recited in claim 2, wherein said heating units each include:

a thin flat metallic heating plate, having one clamping surface disposed to clamp against a flat outer surface of said cartridge;

a thin etched foil electric heater bonded to said flat heating plate on the surface opposite said clamping surface; and a rigid insulator block overlaying said electric heater and attached to said heating plate on the surface opposite said clamping surface.

4. An apparatus for warming blood for transfusion as recited in claim 3, further including spacing means, located within said cartridge, for maintaining proper spacing and parallelism of said cartridge planar members.

5. An apparatus for warming blood for transfusion, comprising:

a fluid-impervious rigid flat metal cartridge defining an enclosed cavity of small volume, having an inlet port and an outlet port at opposite ends thereof, the interior of said cartridge being compatible with the temporary storage of blood, the exterior of said cartridge having two flat heatable surfaces;

said cartridge including a pair of thin metal generally rectangular planar members spaced slightly apart and in parallelism with each other, at least one planar member having on the surface facing the other planar member and running in the direction from inlet port end to outlet port end at least one straight narrow raised ridge of uniform height equal to the distance said members are spaced apart, said planar members being sealed together at their edges to define at least two unobstructed constant-width and uniform-thickness thin ribbon-like conduits for fluid between the interior surfaces of said members;

said cartridge further including a trough-shaped elongated recess defining an inlet chamber communicating with said inlet port, and a trough-shaped elongated recess defining an outlet chamber communicating with said outlet port, each chamber running completely across and communicating with a corresponding end of every conduit, whereby fluid can uniformly flow into and out of each thin ribbon-like conduit across each full conduit width;

heating means including a pair of heating units each having a low thermal mass, a uniform heat flux distribution, and a flat clamping surface disposed to clamp against a corresponding flat outer surface of said cartridge between the inlet and outlet chambers thereof, for heating each of said cartridge heatable surfaces;

temperature sensing means embedded in one of said heating units closely adjacent to said clamping surface, positioned to lie closely adjacent to the outer surface of said cartridge immediately adjacent to the outlet chamber thereof; and control means responsive to said temperature sensing means to control the amount of heat supplied by said heating means to each cartridge flat side.

6. An apparatus for warming blood for transfusion as recited in claim 5, wherein:

said pair of heating units includes a movable heating unit and a fixed heating unit;

said heating means further includes means for supporting said heating units opposite one another with each said clamping surface facing toward and parallel to the other; and said supporting means further includes means releasably clamping said cartridge between and against said supported heating units.

7. An apparatus for warming blood for transfusion as recited in claim 6, wherein said heating units each include:

a thin flat metallic heating plate, having one clamping surface disposed to clamp against a flat outer surface of said cartridge;

a thin etched foil electric heater bonded to said flat heating plate on the surface opposite said clamping surface; and a rigid insulator block overlaying said electric heater and attached to said heating plate on the surface opposite said clamping surface.

* * * * *